(12) United States Patent
Duke (10) Patent No.: US 8,666,488 B2
(45) Date of Patent: Mar. 4, 2014

(54) POST-DOWNLOAD PATIENT DATA PROTECTION IN A MEDICAL DEVICE

(71) Applicant: Physio-Control, Inc., Redmond, WA (US)

(72) Inventor: Steven B. Duke, Bothell, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 13/970,133

(22) Filed: Aug. 19, 2013

(65) Prior Publication Data

US 2013/0333054 A1    Dec. 12, 2013

Related U.S. Application Data

(60) Continuation-in-part of application No. 12/574,380, filed on Oct. 6, 2009, now Pat. No. 8,532,764, which is a division of application No. 11/348,098, filed on Feb. 6, 2006, now abandoned.

(51) Int. Cl.
*A61N 1/00* (2006.01)

(52) U.S. Cl.
USPC ................................. 607/5; 607/30; 607/31

(58) Field of Classification Search
USPC ................................................ 607/5, 30–31
See application file for complete search history.

(56) References Cited

U.S. PATENT DOCUMENTS

| | | | |
|---|---|---|---|
| 4,635,639 A | 1/1987 | Hakala et al. | |
| 4,916,439 A | 4/1990 | Estes et al. | |
| 5,012,411 A | 4/1991 | Policastro et al. | |
| 5,419,336 A | 5/1995 | Margison | |
| 5,499,293 A | 3/1996 | Behram et al. | |
| 5,549,115 A | 8/1996 | Morgan et al. | |
| 5,549,659 A | 8/1996 | Johansen et al. | |
| 5,593,426 A | 1/1997 | Morgan et al. | |
| 5,674,252 A | 10/1997 | Morgan et al. | |
| 5,680,864 A | 10/1997 | Morgan et al. | |
| 5,683,423 A | 11/1997 | Post | |
| 5,683,432 A | 11/1997 | Goedeke et al. | |
| 5,690,690 A | 11/1997 | Nappholz et al. | |
| 5,715,823 A | 2/1998 | Wood et al. | |
| 5,749,902 A | 5/1998 | Olson et al. | |
| 5,749,913 A | 5/1998 | Cole | |
| 5,782,878 A | 7/1998 | Morgan et al. | |
| 5,787,155 A | 7/1998 | Luna | |

(Continued)

FOREIGN PATENT DOCUMENTS

| | | |
|---|---|---|
| EP | 0 801 959 | 10/1997 |
| WO | 00/70889 | 11/2000 |
| WO | 02/060529 | 8/2002 |

*Primary Examiner* — Nicole F Lavert
(74) *Attorney, Agent, or Firm* — Marger Johnson & McCollom PC (57) ABSTRACT

Patient data is stored in a medical device, such as an external defibrillator, and may be transferred, or downloaded, from the medical device to a computing device for storage or analysis. In response to the transfer, the medical device protects the patient data so that at least a subset of users cannot access the patient data from the medical device. The other device to which patient data is transferred from the medical device may be remote from the medical device or may be configured to be part of the medical device. The device to which the patient data is transferred from the medical device can be a remote computing device like a computer or server and/or may include or may be an intermediary data management device (DMD). The medical device may be a wearable medical device, such as a wearable defibrillator or a wearable automatic external defibrillator (AED).

21 Claims, 5 Drawing Sheets

(56) References Cited

U.S. PATENT DOCUMENTS

| | | |
|---|---|---|
| 5,836,993 A | 11/1998 | Cole |
| 5,857,967 A | 1/1999 | Frid et al. |
| 5,891,046 A | 4/1999 | Cyrus et al. |
| 5,891,049 A | 4/1999 | Cyrus et al. |
| 5,899,866 A | 5/1999 | Cyrus et al. |
| 5,921,938 A | 7/1999 | Aoyama et al. |
| 5,950,632 A | 9/1999 | Reber et al. |
| 5,951,485 A | 9/1999 | Cyrus et al. |
| 5,999,493 A | 12/1999 | Olson |
| 6,024,699 A | 2/2000 | Surwit et al. |
| 6,041,257 A | 3/2000 | MacDuff et al. |
| 6,047,207 A | 4/2000 | MacDuff et al. |
| 6,057,758 A | 5/2000 | Dempsey et al. |
| 6,073,049 A | 6/2000 | Alt et al. |
| 6,111,505 A | 8/2000 | Wagener |
| 6,141,584 A | 10/2000 | Rockwell et al. |
| 6,144,922 A | 11/2000 | Douglas et al. |
| 6,150,951 A | 11/2000 | Olejniczak |
| 6,157,713 A | 12/2000 | Emmermann |
| 6,183,417 B1 | 2/2001 | Geheb et al. |
| 6,201,992 B1 | 3/2001 | Freeman |
| 6,301,501 B1 | 10/2001 | Cronin et al. |
| 6,301,502 B1 | 10/2001 | Owen et al. |
| 6,304,780 B1 | 10/2001 | Owen et al. |
| 6,321,113 B1 | 11/2001 | Parker et al. |
| 6,323,782 B1 | 11/2001 | Stephens et al. |
| 6,334,070 B1 | 12/2001 | Nova et al. |
| 6,336,900 B1 | 1/2002 | Alleckson et al. |
| 6,360,120 B1 | 3/2002 | Powers et al. |
| 6,374,138 B1 | 4/2002 | Owen et al. |
| 6,381,492 B1 | 4/2002 | Rockwell et al. |
| 6,405,083 B1 | 6/2002 | Rockwell et al. |
| 6,424,867 B1 | 7/2002 | Snell et al. |
| 6,427,083 B1 | 7/2002 | Owen et al. |
| 6,438,417 B1 | 8/2002 | Rockwell et al. |
| 6,493,581 B2 | 12/2002 | Russell |
| 6,524,241 B2 | 2/2003 | Iliff |
| 6,594,634 B1 | 7/2003 | Hampton et al. |
| 6,597,948 B1 | 7/2003 | Rockwell et al. |
| 6,668,192 B1 | 12/2003 | Parker et al. |
| 6,747,556 B2 | 6/2004 | Medema et al. |
| 6,907,291 B1 | 6/2005 | Snell et al. |
| 7,257,447 B2 | 8/2007 | Cates et al. |
| 2001/0041991 A1 | 11/2001 | Segal et al. |
| 2002/0103508 A1 | 8/2002 | Mathur |
| 2002/0123673 A1 | 9/2002 | Webb et al. |
| 2003/0025602 A1 | 2/2003 | Medema et al. |
| 2003/0058097 A1 | 3/2003 | Saltzstein et al. |
| 2003/0065536 A1 | 4/2003 | Hansen et al. |
| 2003/0095648 A1 | 5/2003 | Kaib et al. |
| 2003/0109904 A1 | 6/2003 | Silver et al. |
| 2003/0212311 A1 | 11/2003 | Nova et al. |
| 2004/0049233 A1 | 3/2004 | Edwards |
| 2004/0212344 A1 | 10/2004 | Tamura et al. |
| 2004/0215278 A1 | 10/2004 | Stegink et al. |
| 2005/0192844 A1 | 9/2005 | Esler et al. |
| 2005/0283210 A1 | 12/2005 | Blischak et al. |
| 2006/0074983 A1 | 4/2006 | Jones |
| 2006/0085040 A1 | 4/2006 | VanDanacker |
| 2006/0206361 A1 | 9/2006 | Logan |
| 2006/0241712 A1 | 10/2006 | Cates et al. |
| 2006/0247710 A1 | 11/2006 | Goetz et al. |
| 2006/0287686 A1 | 12/2006 | Cullen et al. |
| 2008/0058884 A1 | 3/2008 | Matos |

POST-DOWNLOAD PATIENT DATA PROTECTION IN A MEDICAL DEVICE

CROSS-REFERENCE TO RELATED APPLICATIONS

This application is a continuation-in-part of U.S. patent application Ser. No. 12/574,380, filed Oct. 6, 2009, now U.S. Pat. No. 8,532,764, issued on Sep. 10, 2013, which is a division of U.S. patent application Ser. No. 11/348,098, filed Feb. 6, 2006, now abandoned, the entire contents of which are incorporated herein by reference.

TECHNICAL FIELD

The invention relates to medical devices and, more particularly, to medical device data management.

BACKGROUND

An external defibrillator delivers energy to a heart of a patient via electrodes placed upon the patient's chest. Often, external defibrillators are used to deliver energy in the form of a defibrillation pulse to a heart that is undergoing ventricular fibrillation and has lost its ability to properly contract. Ventricular fibrillation is particularly life threatening because activity within the ventricles of the heart is so uncoordinated that virtually no pumping of blood takes place. If untreated, the patient whose heart is experiencing ventricular fibrillation may die within a matter of minutes.

An electrical pulse delivered to a fibrillating heart may depolarize the heart and cause it to reestablish a normal sinus rhythm. In some cases, the patient may need multiple pulses, and an external defibrillator may deliver different quantities of energy with each electrical defibrillation pulse. Further, the defibrillator may provide additional or alternative therapies to the patient, such as cardioversion or pacing therapy. As examples, the external defibrillator may be an automated external defibrillator (AED) used by a first responder or bystander to treat the patient, or a more fully-featured defibrillator/monitor, either manual or automatic, that is used by paramedics.

In some cases, the defibrillator collects and saves information related to the patient. This patient data may include personal and physiological data. Personal data may include the patient's name, age, sex, medical conditions, prescribed medications, or circumstances surrounding the need for treatment with the defibrillator. Physiological data may include the patient's heart rate, blood pressure, electrocardiogram (ECG), or other measured data related to the patient's condition. The patient data may also include a record of therapies provided to the patient, as well as audio recorded during the treatment of the patient. The patient data stored in the defibrillator may be downloaded to another device, such as a computing device for review, generation of a "run report" related to the treatment of the patient, or integration into the patient's long-term medical records.

SUMMARY

The disclosure is directed to techniques for protecting patient data stored in a medical device, such as an external defibrillator. Patient data stored by such devices may be sensitive and personal in nature. Further, the Health Insurance Portability and Accountability Act of 1996 (HIPPA) set for "Standards for Individually Identifiable Health Information," which may apply to at least some patient data stored by such devices. Accordingly, any potential public or unauthorized disclosure of the patient data stored by such medical devices should be avoided.

Some existing external defibrillators and other medical devices store patient data for a potentially indefinite period of time, e.g., until it is overwritten by new patient data. The patient data may be accessible to any user who has physical access to the device. The accessibility of the data may be a particular problem in the case of an automated external defibrillator (AED), which may be physically available to a large pool of trained first responders, or the general public in public locations such as airports, stadiums, shopping malls, or other places of business.

As discussed above, the patient data stored by an external defibrillator may be downloaded to a computing device. Generally, such downloads occur as a matter of course or protocol a short time after the external defibrillator is done being used to treat the patient, e.g., when the first responder returns to a dispatch center or station with an external defibrillator after its use. Further, after such a download, the patient information is generally not needed or used at the external defibrillator.

Accordingly, in response to a download of patient data, embodiments of the invention protect the patient data stored within the external defibrillator. The patient data within the external defibrillator is protected such that it is inaccessible to at least a subset of users that had previously been able to access the data. The protection of the patient data within the external defibrillator may take many forms. For example, patient data within the external defibrillator may be protected by modifying the form of the data, encrypting the data, moving the data to another memory module, password protecting the data, modifying an access control list associated with the patient data, or deleting the data. While the patient data may be deleted as a technique for protecting the data, not deleting the data may allow the data to be recovered at a later time by an authorized user, i.e., a user not part of the subset, if necessary.

The protection of the patient data may occur, but does not necessarily occur upon completion of the download. The protection of the patient data may, for example, occur upon receipt of an acknowledgment from the computing device that downloads the data. Further, the protection may be a user-configurable feature. For example, a user provides an instruction or other input indicating whether the patient data should be protected in response to a download or transfer of data.

Embodiments of the invention may protect patient data stored within the external defibrillator that initially collected the data, as described. Embodiments of the invention may additionally or alternatively protect the patient data collected by an external defibrillator when stored within other medical devices that receive the patient data, such as various medical devices having computing devices or networked servers. The other medical devices may protect the patient data in substantially the same manner described above with respect to the external defibrillator, and in response to further downloading the patient data to yet another device.

In one embodiment, the invention is directed to a method comprising storing patient data collected by an external defibrillator during treatment of a patient in a medical device, allowing users to access the patient data stored in the medical device, downloading the patient data from the medical device to another device and, in response to downloading the patient data, protecting the patient data in the medical device such that the protected patient data is inaccessible to at least a subset of the users.

In another embodiment, the invention is directed to a medical device comprising a memory, a communications circuit and a processor. The memory stores patient data collected by an external defibrillator during treatment of a patient. The communications circuit is configured to communicate with another device. The processor allows users to access the patient data stored in the memory, controls the communications circuit to download the patient data to the other device and, in response to the download, protects the patient data in the memory such that the protected patient data is inaccessible to at least a first subset of the users.

In another embodiment, the invention is directed to a computer readable medium comprising instructions that cause a processor to store patient data collected by an external defibrillator during treatment of a patient within a medical device, allow users to access the patient data stored in the medical device, download the patient data to another device; and in response to the download, protect the patient data in the first device such that the protected patient data is inaccessible to at least a first subset of the users.

In still another embodiment, the invention is directed to a wearable medical device comprising a memory, a communications circuit, and a processor, as described above and having any of the above described features. Such wearable medical devices can themselves be or can be configured to communicate with an external defibrillator and more specifically can be an automatic external defibrillator (AED). As in the above embodiments, the memory of the wearable medical device stores patient data collected by the wearable medical device during treatment of a patient, such as a wearable AED worn by a patient during treatment. The processor of the wearable medical device allows users to access the patient data that is stored in the memory, controls the communications circuit to download the patient data to any other device, and in response to the download, protects the patient data in the memory such that the protected patient data is inaccessible to least a subset of users.

In various embodiments, the disclosure may provide one or more advantages. For example, protecting patient data in a medical device may provide greater security to sensitive information of a patient when multiple users have access to the medical device. Also, protecting the patient data once it is downloaded may allow only a single download of the patient data without further authorization or the intervention of an authorized user.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
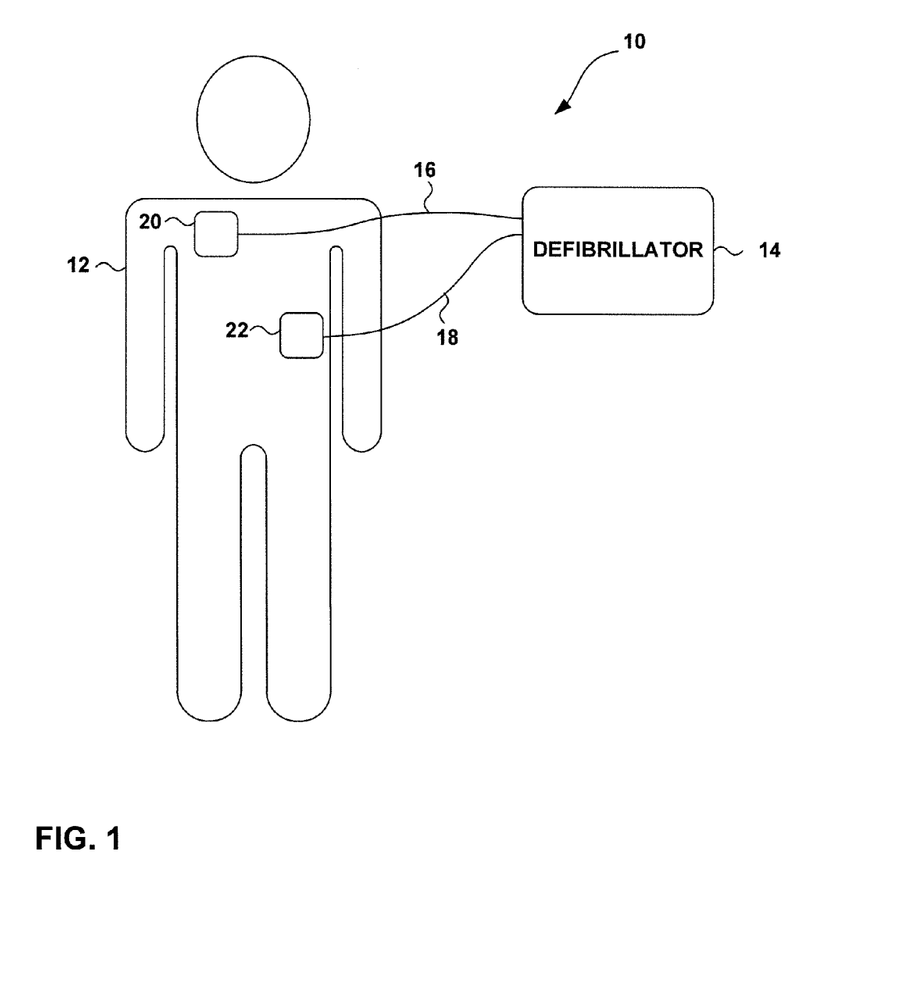
FIG. 1 is a conceptual diagram illustrating an example system that includes an external defibrillator device that collects and stores patient data.

FIG. 1 is a conceptual diagram illustrating an example system 10 that includes an external defibrillator 14 that collects and stores patient data. External defibrillator 14 may, but does not necessarily, take the form of an automated external defibrillator (AED). The AED example system can be in the form of a wearable system that a patient wears for any period of time. A wearable system is any system that can be worn by or a portion of it can be worn by the patient, on the patient's body. In other examples, the example system includes any other medical device that collects and stores patient data.

For example, the wearable system can be a wearable AED that is placed on the patient by a user during emergency treatment of the patient. Alternatively, the wearable system can be a wearable AED that is worn by the patient for treatment lasting a period of time, such as treatment that monitors a patient's health over hours, days, months, or longer, and may prompt or administer treatment based on the patient data that is collected and/or stored. In the wearable AED example system, the patient data can be accessible by the user, the user's medical providers, the manufacturer of the wearable AED, agencies such as the United States Food and Drug Administration (FDA), any testing bodies, and any other authorized user. In some examples, the patient data is accessible by a first subset of users and is inaccessible to a second subset of users. In other examples, the patient data is accessible to any user, but after a portion of the patient data is transferred to another computing device, the patient data becomes protected and inaccessible to some users.

For example, patient data is collected from a patient that wears a wearable AED over a period of time, such as one month. The patient data includes data relating to the patient's health and data relating to how well the wearable AED performed while it was being worn by the patient. While the data is stored in a memory of the wearable AED, any user, including the patient and the patient's medical providers, can access both the patient data relating to the patient's health and the data relating to how well the wearable AED performed while it was being worn by the patient.

At some point in time, perhaps regularly, such as daily or weekly, or manually at the request of a user, some portion or all of the patient data can be transferred to another computing device, such as a remote server or other remote computing system. Upon transfer of the portion or all of the patient data in the other computing device, the patient data that is transferred may or may not be accessible by one or more users at the wearable AED. For example, the portion of the patient data relating to how well the wearable AED performed while being worn by the patient is transferred to the patient's medical provider and the manufacturer of the wearable AED on a weekly basis and to the FDA on a manual basis, as requested. After transfer of the patient data relating to how well the wearable AED performed while being worn by the patient to the patient's medical provider, the manufacturer of the wearable AED, and the FDA, the transferred patient data can be deleted or protected in any suitable way so the patient and/or other users no longer have access to it.

Referring again to FIG. 1, defibrillator 14 is connected to a patient 12 by leads 16 and 18, and electrode pads 20 and 22. Pads 20 and 22 are placed on the bare skin of patient 12, and may be affixed to the patient with an adhesive or any other suitable element or mechanism. Pads 20 and 22 include electrodes through which defibrillator 14 may detect electrical signals within patient 12 and deliver electrical therapy to patient 12. In AED embodiments, external defibrillator 14 may monitor the electrocardiogram (ECG) of patient 12 based on the signals detected via pads 20 and 22, and determine the functionality of the heart. Depending on the condition of the heart, external defibrillator 14 in automated embodiments may deliver instructions to the rescuer such as whether or not to deliver an electrical defibrillation pulse to treat a detected ventricular fibrillation. In other AED embodiments, the defibrillator may automatically deliver a defibrillation pulse based on the ECG analysis. Further, in manual embodiments of defibrillator 14, the rescuer may determine whether a defibrillation pulse should be delivered based on a displayed ECG detected via pads 20 and 22.

Defibrillator 14 may also be capable of monitoring other physiological parameters of patient 12, and delivering other therapies to the patient. For example, defibrillator 14 may include or be coupled to sensors to monitor blood pressure, blood oxygen saturation, respiration, or expired carbon dioxide. Further, defibrillator 14 may be capable of delivering cardioversion or pacing therapies via pads 20 and 22, or controlling delivery of cardiopulmonary resuscitation (CPR) by the rescuer or an automated device.

The patient data collected by defibrillator 14 may include information describing the therapies delivered to patient 12, including the times that the therapies were delivered. The patient data may also include physiological parameter information, including information relating to the times that the physiological parameter information was recorded. In some embodiments, defibrillator 14 may include a microphone or the like through which it may detect audible sound occurring during treatment of patient 12. In such embodiments, defibrillator 14 may include an audio recording as part of the patient data. Defibrillator 14 may collect other personal information of patient 12 such as name, height, weight, age, prescribed medications, medical conditions, location, or any other information that may be desired. This personal information, part of the patient data, may be entered into the defibrillator by the rescuer through the use of a user interface (not shown in FIG. 1).

Figure 2:
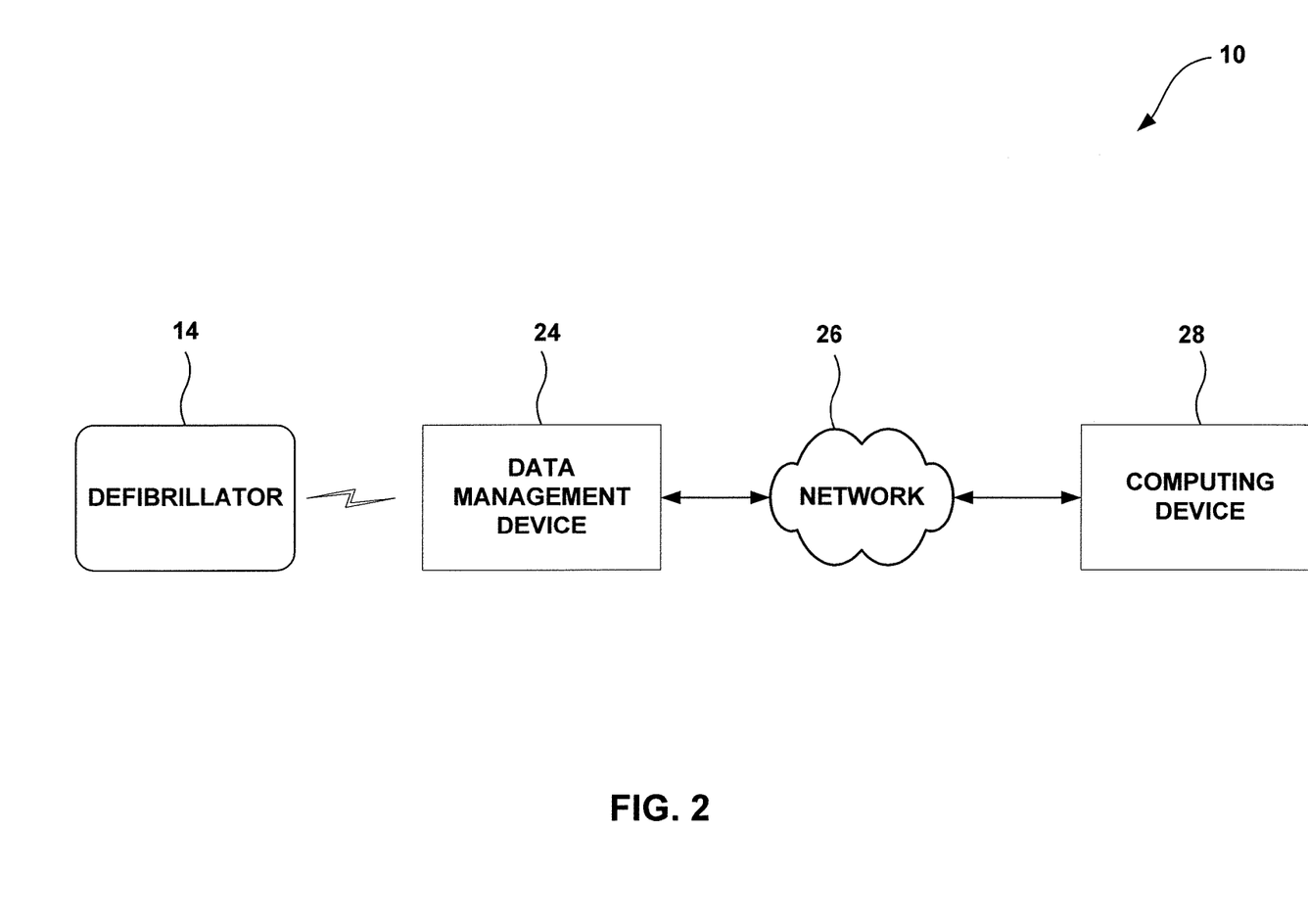
FIG. 2 is a block diagram further illustrating the example system of FIG. 1.

FIG. 2 is a block diagram further illustrating system 10. As discussed above, patient data stored in defibrillator 14 may be downloaded to another device, such as a computing device 28. As examples, the patient data may be downloaded from the defibrillator to the other device for review, generation of a "run report" related to the treatment of the patient, or integration into the long-term medical records of patient 12. Computing device 28 may be any of a variety of devices, such as a handheld, laptop, or desktop computer, or a network server.

In the illustrated embodiment, external defibrillator 14 downloads the patient data to computing device 28 via an intermediate data management device (DMD) 24 and a network 26. Therefore, DMD 24 is an intermediary between defibrillator 14 and computing device 28, and may protect the patient data when the data is transferred between devices in the same or a similar manner to defibrillator 14. DMD 24 may also be a computing device, such as handheld, laptop, or desktop computer, or a network server. Alternatively, DMD 24 may be a base or docking station for the external defibrillator. DMD 24 may have communication circuitry to facilitate local communication with defibrillator 14, as well as network communication with computing device 28.

In the illustrated embodiment, defibrillator 14 and DMD 24 communicate wirelessly, e.g., via an infrared or radio-frequency medium. Nonetheless, the invention is not limited to any particular form of communication between defibrillator 14, DMD 26, network 26 and computing device 28, or any particular form of communication within network 26. Network 26 may be a local area network (LAN) or a wide area network (WAN), such as the Internet.

In some embodiments, DMD 24 may simply forward the patient data to computing device 28. In other embodiments, DMD 24 may store the patient data, and may also provide functionality associated herein with computing device 28, such as generation of run reports, or other processing or management of the patient data. Further, in some embodiments, DMD 24 may allow additional patient data to be entered by a user and combined with the patient data collected by defibrillator 14. For example, DMD 24 may be a handheld or other type of computing device used by an emergency medical technician (EMT) or first responder to input patient data during or after treatment of patient 12, and to combine the inputted data with patient data downloaded from defibrillator 14 during or after treatment of patient 12.

Further, in some embodiments, computing device 28 may download the patient data to other devices. For example, computing device 28 may take the form of a network server that downloads the data to a particular computer or system, which may be associated with a hospital or a manufacturer of defibrillator 14, for archival, review by clinicians or engineers, or integration into the long-term medical records of patient 12. Moreover, other embodiments need not include network 26 or DMD 24. In such embodiments, defibrillator 14 may simply download patient data directly to computing device 28.

In any event, in response to a download of patient data from defibrillator 14 to another device, such as DMD 24 or computing device 28, defibrillator 14 protects the patient data stored in the defibrillator. More particularly, defibrillator 14 protects the patient data such that at least a subset of users who could previously access the patient data stored in the defibrillator are no longer able to access the patient data in the defibrillator. The protection of the patient data may occur, but does not necessarily occur upon completion of the download from defibrillator 14. Defibrillator 14 may, for example, protect the patient data upon receipt of an acknowledgment from DMD 24 or computing device 28 that the data has been successfully downloaded. When protected, the patient data may be inaccessible via a user interface of defibrillator 14 and/or via computing devices that communicate with the defibrillator.

Defibrillator 14 may protect the patient data stored therein in a variety of ways. For example, defibrillator 14 may protect the patient data therein by modifying the form of the data, encrypting the data, moving the data to another memory module, password protecting the data, modifying an access control list associated with the patient data, or deleting the data. When defibrillator 14 protects the patient data by deleting the patient data, the patient data is no longer available to any users via the defibrillator. However, when defibrillator 14 protects the patient data using other techniques, a subset of users may be able to unprotect the patient data or otherwise recover the protected data.

Patient data protection may be a user-configurable feature of defibrillator 14. In other words, a user may provide an instruction or other input indicating whether the patient data should be protected in response to a download. For example, whether patient data will be protected in defibrillator 14 in response to a download of the patient data may be a user selectable option in a menu of configuration options displayed by the defibrillator via a user interface. Defibrillator 14 may also allow the user to configure various sub-options related to patient data protection. For example, defibrillator 14 may allow a user to select whether patient data will be protected only in response to receiving an acknowledgment from a downloading device, or which patient data protection techniques will be used to protect data. Defibrillator 14 may also allow a user to set a password for accessing protect patient data or identify a subset of users who will be able to access protected data.

Further, other medical devices may be able to protect patient data in the manner described herein with respect to defibrillator 14. For example, if DMD 24 stores patient data, DMD 24 may protect patient data in the manner described herein in response to downloading the patient data to computing device 28 via network 26. DMD 24 may keep or destroy a local copy of the patient data after the data is sent, depending on the configuration of the DMD. DMD 24 may be configured to protect patient data, e.g., by modifying or deleting the data, in the same manner as defibrillator 14. Therefore, the patient data may be protected in DMD 24 as desired by a user. Further, if computing device 28 stores patient data, the computing device may protect patient data in the manner described herein in response to downloading the patient data to another device.

Figure 3:
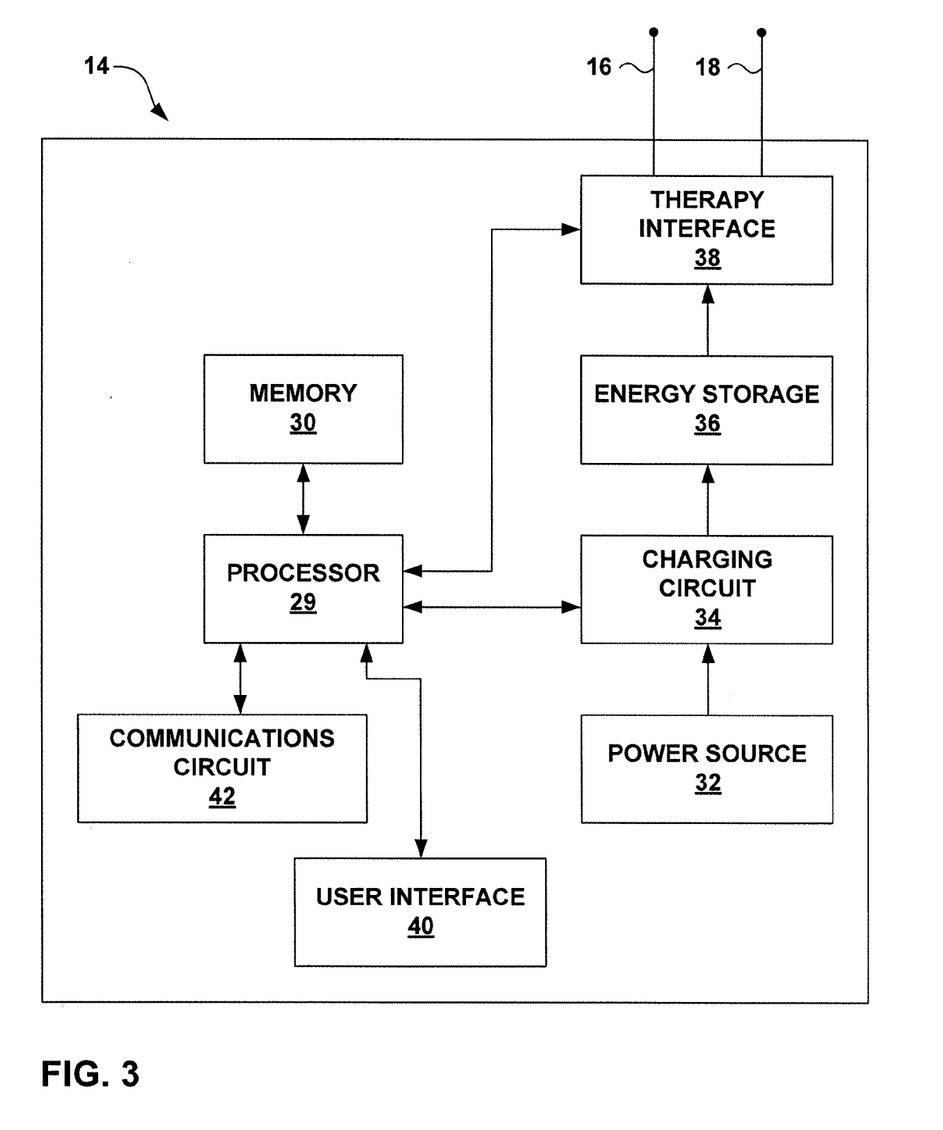
FIG. 3 is a functional block diagram illustrating components of the external defibrillator of FIG. 1.

FIG. 3 is a functional block diagram illustrating components of external defibrillator 14. As shown in FIG. 3, defibrillator 14 may include a processor 29, memory 30, power source 32, charging circuit 34, energy storage 36, therapy interface 38, user interface 40, and communications circuit 42. Leads 16 and 18 are coupled to therapy interface 38.

Processor 29 controls the operations of defibrillator 14 based upon the instructions located in memory 30. Processor 29 controls charging circuit 34 to draw current from power source 32 to charge energy storage circuit 36. Processor 29 controls whether therapy interface 38 detects electrical signals from patient 12, or is coupled to energy storage circuit 36 to deliver the energy stored therein to patient 12 as a defibrillation pulse. Processor 29 also provides prompts and other information to a rescuer, and receives information and commands from a rescuer through user interface 40. Processor 29 sends and receives information to or from other devices though communications circuit 42. Further, as will be discussed in greater detail below, processor 29 stored patient data in memory 30, and protects the patient data in response to downloading the patient data to another device, such as DMD 24 or computing device 28, via communications circuit 40.

Memory 30 stores instructions that cause processor 29 to provide the functionality ascribed to it and defibrillator 14 herein. Memory 30 may include any one or more of a random access memory (RAM), read-only memory (ROM), electronically-erasable programmable ROM (EEPROM), flash memory, or the like. Memory 30 may be fixed within AED 26 or removable from the AED. Processor 29 may comprise any one or more of a microprocessor, digital signal processor (DSP), application specific integrated circuit (ASIC), field-programmable gate array (FPGA), or other digital logic circuitry.

In a typical application, interface 38 includes a receptacle and conductors 16 and 18 plug into the receptacle. Interface 38 also includes a switch (not shown in FIG. 3) that, when activated, couples an energy storage circuit 36 to conductors 16 and 18. Energy storage circuit 36 stores the energy to be delivered to patient 12 in the form of a defibrillation pulse. The switch may be of conventional design and may be formed, for example, of electrically operated relays. Alternatively, the switch may comprise an arrangement of solid-state devices such as silicon-controlled rectifiers or insulated gate bipolar transistors.

Energy storage circuit 36 includes components, such as one or more capacitors, that store the energy to be delivered to patient 12 via conductors 16 and 18 and electrodes 20 and 22 (FIG. 1). Before a defibrillation pulse may be delivered to patient 12, energy storage circuit 36 must be charged. Processor 29 directs a charging circuit 34 to charge energy storage circuit 36 to a high voltage level. Charging circuit 34 comprises, for example, a flyback charger that transfers energy from power source 32 to energy storage circuit 36.

Defibrillator 14 may be a manual defibrillator or an AED. Where defibrillator 14 is a manual defibrillator, a caregiver using defibrillator 14 may select an energy level for each defibrillation pulse delivered to patient 12. Processor 29 may receive the selection made by the caregiver via a user interface 40, which may include input devices, such as a keypad and various buttons or dials, and output devices, such as various indicator lights, a cathode ray tube (CRT), light emitting diode (LED), or liquid crystal display (LCD) screen, and a speaker. In some embodiments, user interface 40 may include a touch-sensitive display. Where defibrillator 14 is an AED, processor 29 may select an energy level from a preprogrammed progression of energy levels stored in memory 30 based on the number of defibrillation pulses already delivered to patient 28.

When the energy stored in energy storage circuit 36 reaches the desired energy level, processor 29 controls user interface 40 to provide an indication to the caregiver that defibrillator 14 is ready to deliver a defibrillation pulse to patient 12, such as displayed indication or a voice prompt. The defibrillation pulse may be delivered manually or automatically. Where the defibrillation pulse is delivered manually, the caregiver may direct processor 29 to deliver the defibrillation pulse via user interface 40 by, for example, pressing a button. In either case, processor 29 activates the switches of interface 34 to electrically connect energy storage circuit 36 to electrodes 20 and 22, and thereby deliver the defibrillation pulse to patient 12.

Processor 29 may modulate the defibrillation pulse delivered to patient 12. Processor 29 may, for example, control the switches of interface 38 to regulate the shape and width of the pulse. Processor 29 may control the switches to modulate the pulse to, for example, provide a multiphasic pulse, such as a biphasic truncated exponential pulse, as is known in the art.

Processor 29 may perform other functions as well, such as monitoring electrical activity of the heart of patient 12 sensed via electrodes 20 and 22. Processor 29 may determine whether the heart of patient 12 is fibrillating based upon the sensed electrical activity in order to determine whether a defibrillation pulse should be delivered to patient 12. Where a defibrillation pulse has already been delivered, processor 29 may evaluate the efficacy of the delivered defibrillation pulse by determining if the heart is still fibrillating in order to determine whether an additional defibrillation pulse is warranted. Processor 29 may automatically deliver defibrillation pulses based on these determinations, or may advise the caregiver of these determinations via user interface 40. Processor 29 may display an electrocardiogram (ECG) that reflects the sensed electrical activity via user interface 40.

Processor 29 may store an indication of the time of delivery of each defibrillation pulse delivered to patient 12 as patient data within memory 30 for patient 12. Processor 29 may also store the energy level of each pulse and other characteristics of each pulse, such as the width, amplitude, or shape, as patient data. Processor 29 may also store a digital representation of the ECG, or a heart rate over time determined based on the electrical activity of the heart of patient 12 detected via electrodes 20 and 22 as patient data. Further, processor 29 may control delivery of other types of therapy to patient 12 via electrodes 20 and 22, such as cardioversion or pacing therapy, and store information describing the times that such therapies were delivered and parameters of such therapies, such as cardioversion pulse energy levels and pacing rates, as patient data for patient 12.

User interface 40 may include a microphone (not shown) that detects sounds in the vicinity of defibrillator 14. Processor 29 may receive signals from the microphone and store an audio recording that includes these signals as patient data. The audio recording may include verbal notations of a user of defibrillator 14, or conversations between the user and patient 12.

The user may mark the time of the occurrence of various events, such as the delivery of drugs or the administration of cardiopulmonary resuscitation (CPR), during the treatment of patient 12 by, for example, pressing a key or button of user interface 40 at the time when the event occurred. Processor 29 may also include these event markers within the patient data stored in memory 30. Where defibrillator 14 is more fully featured, e.g., a manual paramedic or hospital defibrillator, defibrillator 14 may also include additional sensors (not shown) coupled to processor 29, such as sensors to measure blood oxygen saturation, blood pressure, respiration, and the amount of oxygen or carbon dioxide in the air inhaled or exhaled by patient 12. Processor 29 may also store the signals generated by these sensors within memory 30 as patient data for patient 12. In other words, as examples, processor 29 may also store any of a capnograph, a plethysmograph, a blood oxygen saturation over time, a blood pressure over time, a pulse rate over time determined based on measured blood pressure, end tidal carbon dioxide measurements, and/or measurements of the fraction of carbon dioxide in air inspired or expired within memory 30 as patient data. Processor 29 may begin to store patient data when defibrillator 14 is powered on to respond to a medical emergency.

Communications circuit 42 may be used as an interface between defibrillator 14 and another device, such as DMD 24 or computing device 28. Communications may be accomplished through wired or wireless connections. Wired communication connections may include a universal serial bus (USB), a FireWire connection (IEEE 1394), a serial connection, Ethernet connection, modem connection, or any other wired communication technique. Wireless communications may be accomplished by radio frequency (RF) or infrared communication, such as communication according to the Bluetooth, IEEE 802.11 or IRDA protocols.

Power source 32 delivers operating power to the components of AED 26. Power source 32 may include a large battery and a power generation circuit to produce the operating power and therapy. In some embodiments, the battery may be rechargeable to allow extended operation. Recharging may be accomplished by drawing current from a standard alternating current electrical outlet, such as a 120 V outlet. In some embodiments, power source 32 may run directly off of an alternating current outlet.

The patient data stored in memory 30 by processor 29 may include information describing the therapies delivered to patient 12, including the times that the therapies were delivered. The patient data may also include physiological parameter information, including information relating to the times that the physiological parameter information was recorded. The patient data may also include patient personal and identification information, as well as an audio recording.

Processor 29 protects the patient data for patient 12 within memory 30 in response to downloading the patient data to another device via communications circuit 42. Processor 29 protects the patient data such that it is not accessible to at least a subset of users of defibrillator 14. Processor 29 may delete the patient data from memory 30 such that it is no longer available to any users. In other embodiments, processor 29 protects the patient data from being accessed by a first subset of users, but leaves the patient data accessible by a second subset of users. The second subset of users may be a limited number of users, which may be similar to administrative users in the context of a network. The second subset of users may be owners of defibrillator 14, or agents of the manufacturer of defibrillator 14.

In some embodiments, processor 29 modifies, or changes, the data structure of the patient data within memory 30 to a form not readable by DMD 24 or other computing devices that communicate with defibrillator 14. In some embodiments, processor 29 encrypts and/or password protects the patient data such that only the second subset of users, e.g., those who have a password and/or a key to unencrypt the patient data, can access the patient data. Processor 29 may encrypt the patient data with an algorithm stored in memory 30. A password may be entered by a user via user interface 40, or using a computing device via communications circuit, and may be an alphanumeric password or key combination. In other embodiments, a password may be machine-readable, e.g., may be read by defibrillator 14 from a magnetic or radio-frequency identification card.

In some embodiments, user access to at least some of the functionality and resources provided by defibrillator 14 may be controlled by user identification and/or passwords. The user identification or passwords may be alphanumeric, key combination or machine readable. In such embodiments, processor 29 may maintain access control lists (ACLs) in memory 30 for resources of defibrillator 14, including patient data for patient 12 stored in memory 30, associating users or classes of users with a degree of access provided to the user or class for that resource. In such embodiments, processor 29 may protect the patient data for patient 12 by modifying an ACL for the patient data to change the degree of access for a subset of users or classes, and thereby prevent the subset of users from accessing the patient data.

Figure 4:
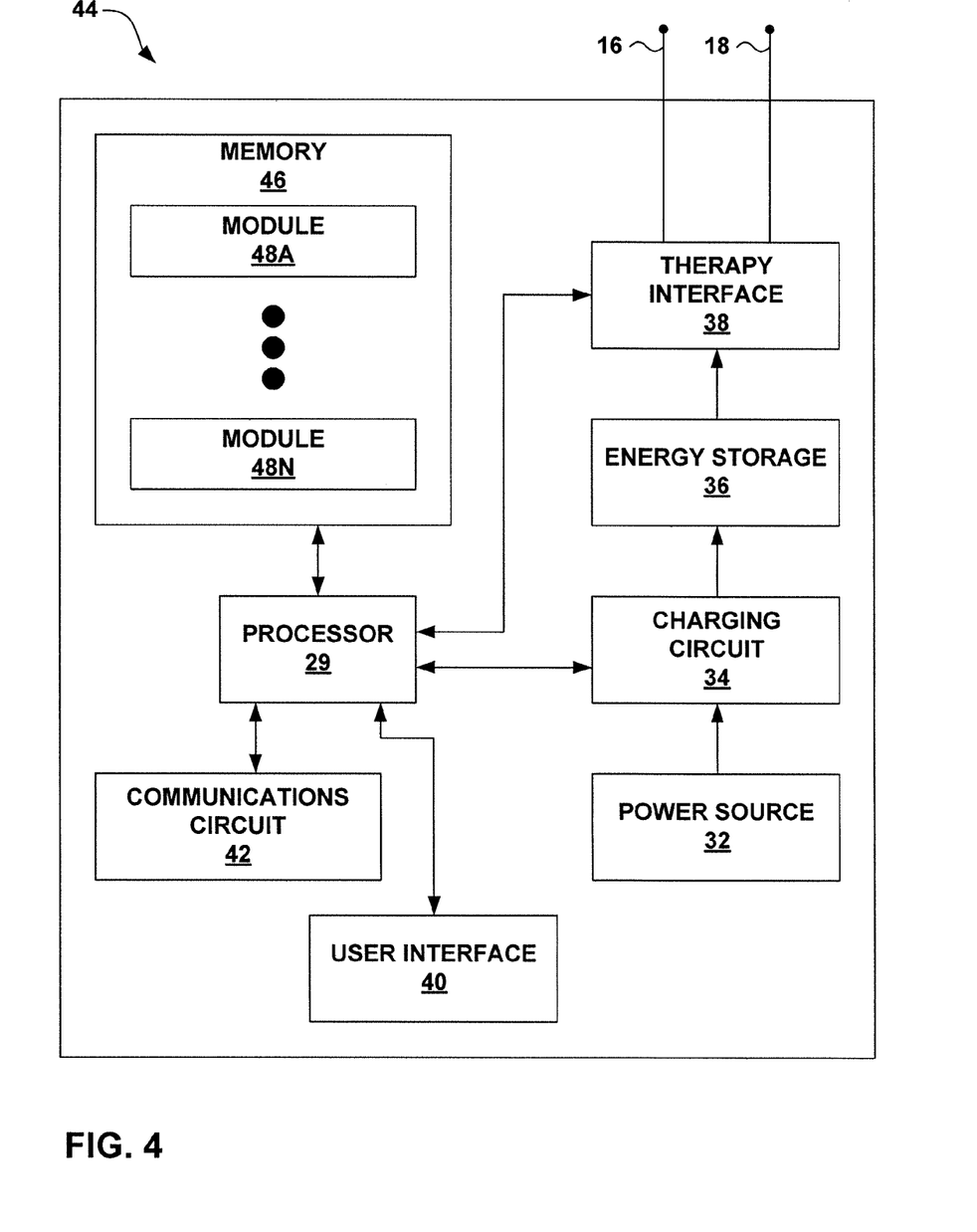
FIG. 4 is functional block diagram illustrating components of another example external defibrillator that collects and stores patient data, the defibrillator including multiple memory modules.

FIG. 4 is functional block diagram illustrating components of another example external defibrillator 44 that collects and stores patient data. Like defibrillator 14, defibrillator 44 may include processor 29, power source 32, charging circuit 34, energy storage circuit 36, therapy interface 38, user interface 40 and communications circuit 42, which are substantially similar to the like-numbered components described above with reference to FIG. 3 and defibrillator 14.

In general, memory 46 is similar to memory 30. However, in the example of FIG. 4, memory 46 is made up of a plurality of modules 48A-48N (collectively, "modules 48"). Modules 48 may, but are not necessarily, physically different circuits for storing data.

In the embodiment illustrated by FIG. 4, processor 29 may store patient data in one of modules 48 during therapy. Once DMD 24 or another device downloads the patient data, processor 29 protects the patient data by moving the patient data to another of modules 48. The other module may be "hidden" or otherwise protected from being accessed by a subset of users via user interface 40 or communications circuit 42. For example, access to the protected module may be protected by a password and/or ACL.

Figure 5:
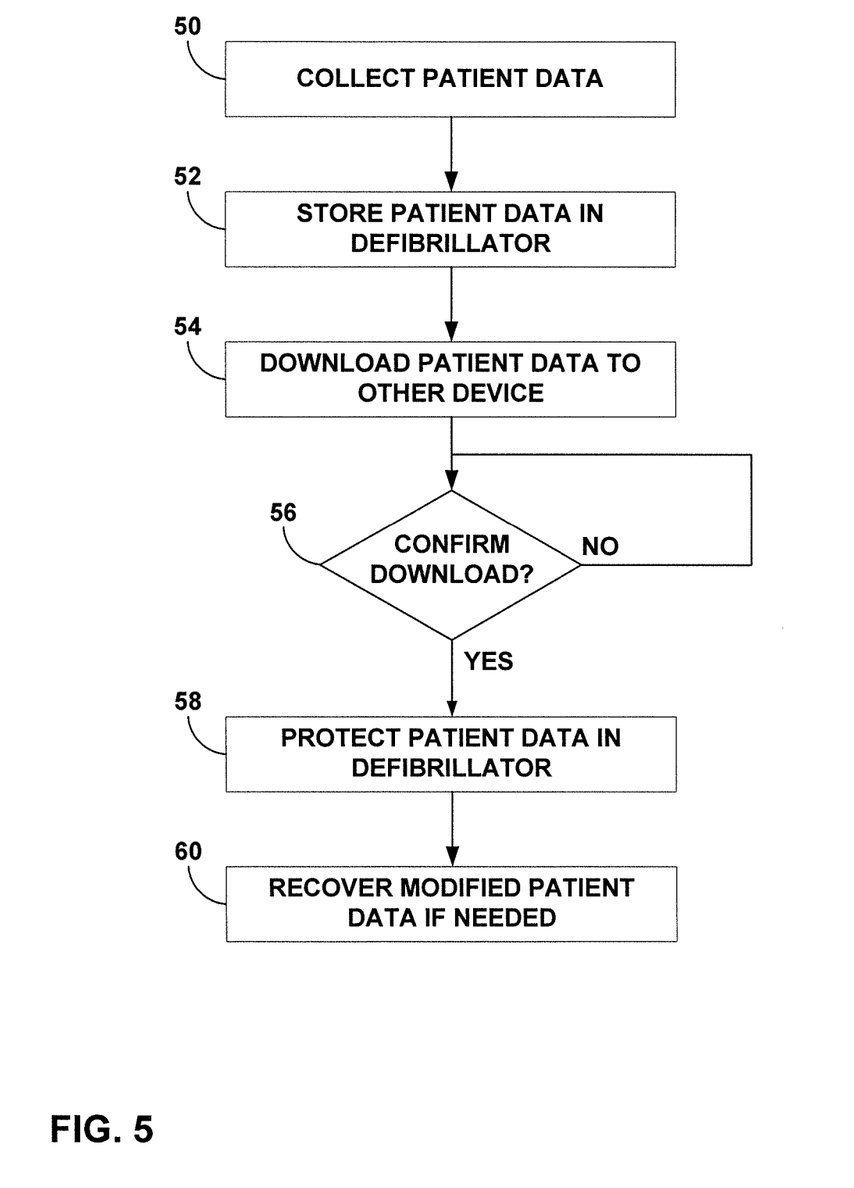
FIG. 5 is a flow diagram illustrating an example technique for protecting patient data stored in an external defibrillator.

FIG. 5 is a flow diagram illustrating an example technique for protecting patient data stored in an external defibrillator. Either of defibrillators 14 and 44 may be used in the example of FIG. 5 or a wearable defibrillator can be used, but defibrillator 14 will be used as an example. Defibrillator 14, and more particularly processor 29 of defibrillator 14, collects patient data for patient 12 during the treatment of the patient (50). The patient data may include medical and personal information for patient 12, as discussed in greater detail above. Processor 29 stores the patient data in memory 30 for reference during treatment of patient 12 or review (52). Processor 29 downloads the patient data to DMD 24, or to computing device 28 directly via DMD 24 via communications circuit 42 (54). Processor 29 may download the patient data in response to a request from a user received via user interface 40.

In the example illustrated by FIG. 5, processor 29 waits for a confirmation that the download of patient data to DMD 24 was successful (56). The confirmation may be, as examples, a confirmation data packet sent by DMD 24, or a positive cyclical redundancy check (CRC). When processor 29 confirms a successful download, the processor protects the patient data sent to DMD 24 in the memory 30 using any one or more of the techniques discussed in greater detail above (58). In some embodiments, once the patient data is modified, a first subset of users cannot access the patient data, which a second subset of users may access, e.g., recover, the patient data if necessary (60).

The invention is not limited to embodiments in which processor 29 confirms a successful download prior to protecting the patient data. In some embodiments, processor 29 protects the patient data in response to initiation of the transfer of data to DMD 24. In some embodiments, processor 29 protects the patient data in response to completion of the transfer of data to DMD 24 without confirming that the download was successful. In some embodiments, processor 29 protects the patient data for some time period, which may or may not be predetermined, after the download begins or ends.

Further, as discussed above, other medical devices may protect patient data in response to downloading the patient data to another device in a substantially similar manner to that described herein with respect to defibrillators 14 and 44. For example, DMDs 24 and computing devices 28 may protect patient data as described herein. Although such devices may not include therapy or monitoring components specific to a defibrillator and illustrated in FIGS. 3 and 4 with respect to defibrillators 14 and 44, the devices may include processors 29, memories 30 or 46, user interfaces 40 and communication circuitry 42 that provide the functionality described above with respect to protection of patient data.

Many embodiments of the invention have been described. Various modifications may be made to the described embodiments without departing from the scope of the claims. These and other embodiments are within the scope of the following claims.

The invention claimed is:

1. A system, comprising:
   a computing device; and
   a medical device having:
   a memory configured to store patient data collected by the medical device during treatment of a patient,
   a communications circuit configured to communicate with the computing device, and
   a processor that allows users to access the patient data stored in the memory, controls the communications circuit to transfer the patient data to the computing device, and, in response to the transfer, protects the patient data in the memory by making the patient data inaccessible to at least a subset of the users, wherein, to protect the patient data, the processor makes the data inaccessible to a first subset of authorized users while leaving the patient data accessible to a second subset of authorized users, wherein the patient data was accessible to the first subset of authorized users before the patient data was protected.

2. The system of claim 1, wherein the computing device comprises a data management device.

3. The system of claim 2, wherein the data management device is configured to generate a run report related to treatment of the patient, integrate the patient data with existing medical records associated with the patient, or both.

4. The system of claim 1, wherein the computing device comprises at least one of a handheld computing device, a laptop computer, a desktop computer, or a server.

5. The system of claim 1, wherein the computing device is configured to protect the transferred patient data.

6. The system of claim 5, wherein the computing device is configured to protect the transferred patient data by preventing access to the transferred patient data by the first subset of users.

7. The system of claim 1, further comprising a data management device that has communication circuitry configured to facilitate transferring the patient data between the medical device and the data management device and between the data management device and the computing device.

8. The system of claim 7, wherein the data management device protects the patient data during the transfer of the patient data between the medical device and the data management system and between the data management system and the computing device.

9. The system of claim 7, wherein the data management device comprises at least one of a base, a docking station, or both for the medical device.

10. The system of claim 7, wherein the data management device includes a data management computing device comprising at least one of a handheld computing device, a laptop computer, a desktop computer, or a server.

11. The system of claim 7, wherein the data management device is configured to generate a run report related to treatment of the patient, integrate the patient data with long-term medical records associated with the patient, or both.

12. The system of claim 7, wherein the data management device includes a data management device memory that stores at least a portion of the patient data that is transferred from the medical device.

13. The system of claim 7, wherein the data management device includes an input device that is configured to receive data management device input data from a user, the data management device input data relates to the patient and is additional to or a modification of the patient data transferred from the medical device to the data management device.

14. The system of claim 13, wherein the data management device input data is input by the user after treatment of the patient.

15. The system of claim 13, wherein the data management device input data is input by the user during treatment of the patient.

16. The system of claim 1, wherein the communications circuit is configured to wirelessly communicate with the computing device.

17. The system of claim 1, wherein the computing device is a first computing device that is configured to transfer the patient data to a second computing device.

18. The system of claim 17, wherein the first computing device is a network server and the second computing device is a remote computing system.

19. The system of claim 1, wherein the processor protects the patient data in the memory after receiving an acknowledgement from the computing device that the transfer of the patient data is successful.

20. The system of claim 1, wherein the medical device is configured to permit a user to input an instruction to the processor that indicates whether the patient data should be protected in response to the transfer of the patient data.

21. The system of claim 1, wherein the computing device and the medical device communicate over a network.

* * * * *